(12) United States Patent
Yoo et al.

(10) Patent No.: US 6,316,641 B1
(45) Date of Patent: Nov. 13, 2001

(54) METHOD FOR PRODUCING AN EPOXIDE, IN PARTICULAR OF GLYCIDOL, AND INSTALLATION FOR IMPLEMENTATION

(75) Inventors: Jeong-Woo Yoo; Zéphirin Mouloungui; Antoine Gaset, all of Toulouse (FR)

(73) Assignee: Organisation Nationale Interprofessionelle des Oleagineux (O.N.I.D.OL.), Paris (FR)

( * ) Notice: Subject to any disclaimer, the term of this patent is extended or adjusted under 35 U.S.C. 154(b) by 0 days.

(21) Appl. No.: 09/380,710
(22) PCT Filed: Mar. 6, 1998
(86) PCT No.: PCT/FR98/00451
 § 371 Date: Sep. 8, 1999
 § 102(e) Date: Sep. 8, 1999
(87) PCT Pub. No.: WO98/40371
 PCT Pub. Date: Sep. 17, 1998

(30) Foreign Application Priority Data

Mar. 12, 1997 (FR) .................................................. 97 03163

(51) Int. Cl.⁷ ........................ C07D 301/02; C07D 301/32
(52) U.S. Cl. ........................................... 549/519; 549/541
(58) Field of Search ...................... 549/519, 541

(56) References Cited

U.S. PATENT DOCUMENTS

| | | |
|---|---|---|
| 2,636,040 | 4/1953 | Brunson . |
| 2,856,413 | 10/1958 | Malkemus et al. . |
| 3,625,981 | 12/1971 | Kollar . |
| 4,265,821 | 5/1981 | McEntire et al. . |
| 4,276,223 | 6/1981 | Wu . |
| 4,374,259 | 2/1983 | McEntire . |
| 4,387,237 | 6/1983 | Renga et al. . |
| 5,003,115 | 3/1991 | Strutz . |

FOREIGN PATENT DOCUMENTS

| | | |
|---|---|---|
| 2037703 | 4/1971 | (DE) . |
| 0 047 474 | 3/1982 | (EP) . |
| 0 180 387 | 5/1986 | (EP) . |
| 0 193 228 | 9/1986 | (EP) . |

*Primary Examiner*—Taofiq A. Solola
(74) *Attorney, Agent, or Firm*—Young & Thompson

(57) ABSTRACT

The invention concerns a method for preparing an epoxide, in particular glycidol, wherein a cyclic organic carbonate, in particular glycerol carbonate, is heated under reduced pressure so as to carry out a reaction to contract the carbonate ring into an epoxide ring. According to the present invention, the reaction is carried out in a solid/liquid system in the presence of a polyol and a solid catalyst consisting of a type A zeolite or γ-alumina. The method, which may be carried out continuously, enables the epoxide to be formed in a single step, the epoxide being exhausted in the form of vapor which only has to be extracted and separated from the carbon dioxide formed.

12 Claims, 3 Drawing Sheets

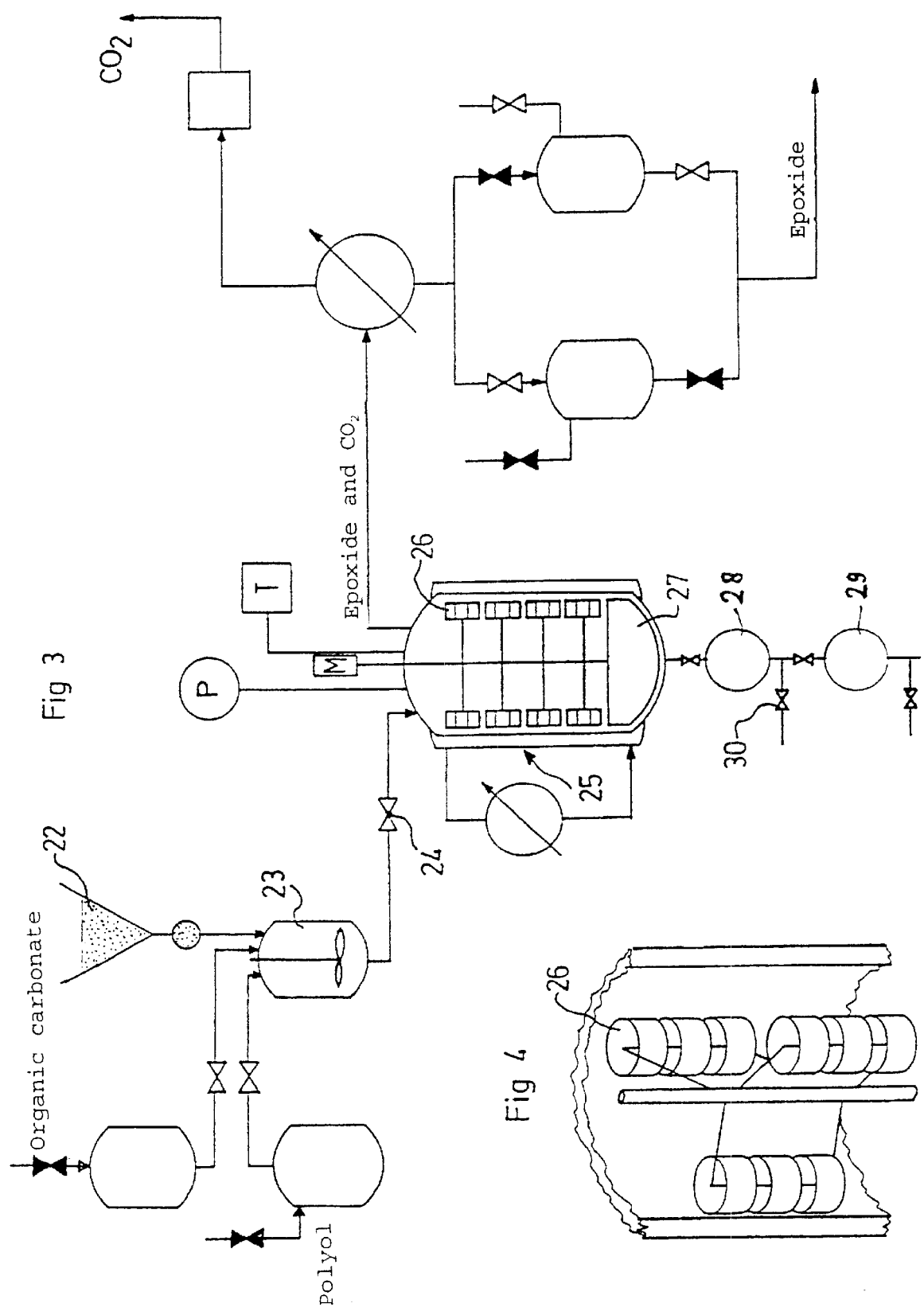

METHOD FOR PRODUCING AN EPOXIDE, IN PARTICULAR OF GLYCIDOL, AND INSTALLATION FOR IMPLEMENTATION

This application is a 371 of PCT/FR98/00451 filed Mar. 6, 1998.

The invention concerns a method for preparing an epoxide of the formula:

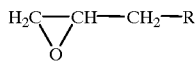

where R is a hydroxyl OH group for glycidol,
or an alkoxide radical O—R' with R'=alkyl or acyl for glycidyl compounds,
or a hydrogen H or an alkyl group for alkylene oxides.

The invention applies in particular to the preparation of glycidol:

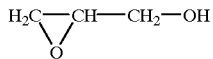

or glycidyl compounds (in which the hydrogen of hydroxyl is replaced by an alkyl or acyl radical).

Epoxides have many applications as adhesives, coatings, intermediate products for the preparation of polyurethanes etc. Glycidol and its glycidyl derivatives are one of the important epoxide families and are used to a considerable extent in the textile, plastics, pharmaceutical, cosmetics and photochemical industries, in the detergents industry, and in building and public works by reason of their properties as stabilizers, plastics modifiers, surfactants and fire retardants etc. Since the start of the 1970s, glycidol has been produced industrially by oxidizing allyl alcohol by means of hydrogen peroxide in the presence of a catalyst based on tungsten oxide. The essential defect in this method lies in the large number of steps necessary for obtaining the aforementioned oxidation, for extracting glycidol from the homogeneous aqueous medium (containing the starting reagent and several byproducts: glycerol, acrolein, betahydroxypropionaldehyde, glycerol allyl ether and decomposition products of the catalyst) and for then purifying the glycidol obtained in the aqueous medium. Moreover, the catalyst based on tungsten oxide is decomposed during the reaction and its consumption is a factor in increasing the cost (DE-OS 2 037 703, U.S. Pat. No. 3,625,981).

It should be noted that, before this method of preparation from allyl alcohol, other methods had been proposed for preparing glycidol, either from glycerol and ethylene carbonate, propylene carbonate or butylene carbonate (U.S. Pat. No. 2,636,040), or from glycerol carbonate (U.S. Pat. No. 2,856,413). If such preparations could be transposed onto the industrial scale, they would be particularly interesting since the starting products can easily be obtained from oleaginous plant materials, thus offering an outlet for these materials. However, the method proposed in the first patent (U.S. Pat. No. 2,636,040) which consists of preparing an intermediate complex from ethylene carbonate, propylene carbonate or butylene carbonate, and decomposing this, has the drawback of requiring a succession of steps with different operating conditions, certain of these at very low pressures; moreover, the effective yield from the method is relatively low (63%). The method dealt with in the second patent (U.S. Pat. No. 2,856,413) which consists of decomposing glycerol carbonate and then synthesizing glycidol in the presence of a metal salt dissolved in the glycerol carbonate, also has the drawback of requiring successive steps with different operating conditions (decomposition at a very low pressure, synthesis of glycidol and distillation); the same comments may be formulated as previously. In addition, the inventors of the present invention have carried out tests under the conditions of this patent and have found that, during the reaction, a very adherent solid polymer is formed which is deposited on the walls of the reactor and gradually blocks it.

The object of the invention is to provide a method for preparing glycidol or a glycidyl compound, or in a more general manner an epoxide of the formula previously indicated from a cyclic organic carbonate, in particular glycerol carbonate or a derivative of this compound, which can be employed in a single step, in particular continuously, and which is able to operate at pressures above the reduced pressures called for in the methods described above.

Another objective is to obtain a high effective yield (the effective yield being defined by the number of moles of epoxide recovered to the number of moles of cyclic organic carbonate used).

Another objective is to isolate the epoxide directly, in particular glycidol or glycidyl compound, and to anticipate a high purity for this compound.

To this end, the method with which the invention is concerned uses as the starting compound a cyclic organic carbonate with 5 links having the formula:

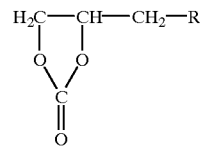

where
R=OH (for glycerol carbonate)
R=H for propylene carbonate,
R=alkyl for alkylene carbonates,
R=O—R' with R'=alkyl or acyl for other cyclic organic carbonates.

The method concerned is of the type in which the cyclic organic carbonate is heated under reduced pressure to a temperature at least equal to 165° C. so as to carry out a contraction reaction of the carbonate ring:

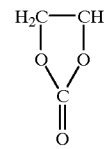

into an apoxy ring

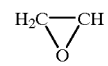

The method of the invention is characterized in that the reaction is carried out in a solid/liquid system in the presence of a polyol and a solid catalyst consisting of a type A zeolite or γ-alumina.

In the process of the invention, the reaction used makes it possible to form, in a single step (and therefore with a single set of operating conditions), the epoxide, in particular glycidol or a glycidyl derivative, which is exhausted in the form of vapor and which only has to be extracted and separated from the carbon dioxide formed (simply by condensation). An epoxide is obtained directly in this way with good purity (greater than 92%). This reaction may be easily employed continuously by continuous extraction of the gaseous phase and continuous separation by condensation. Experiments showed, particularly in the case of the preparation of glycidol, that the reaction did not require very stringent low pressures and could in particular be carried out at pressures substantially between $3 \times 10^3$ and $10 \times 10^3$ Pascals at temperatures substantially between 170° C. and 210° C.; in particular, a pressure range of between $3.3 \times 10^3$ and $6 \times 10^3$ Pascals gave excellent performances while leading to moderate industrial operating costs. Tests have shown that the effective yield of epoxide was of the order of 75% to 90%.

The method of the invention is accordingly characterized by the presence in the reaction medium of:
- on the one hand, a polyol which can advantageously consist of glycerol or a polyglycerol,
- on the other hand, a specific solid catalyst: A-type zeolite, preferably in the H (wherein cation is replaced by $H^+$) form or containing an alkali metal or alkaline earth cation, or γ-alumina.

The mechanisms which lead to the epoxide under the operating conditions of the method of the invention are novel in the type of reaction concerned. First of all, the polyol fulfils a first function of being a carrier for the organic carbonate, preventing decomposition of this compound at the temperature of the medium and enabling it to diffuse and access the catalytic sites of the zeolite or γ-alumina ; the organic carbonate may thus be adsorbed on the catalytic sites of the zeolite or of the γ-alumina. Once the organic carbonate is adsorbed on these catalytic sites it is able to open, taking into account the pressure and temperature of the medium, and the polyol then fulfils a second function of a proton donor enabling this opening and contraction of the carbonate ring into an epoxy ring to occur. The epoxide thus formed is gaseous at the pressure and temperature of the medium and diffuses outside the catalytic site. Moreover, no tarry deposit is observed during or at the end of the process and it seems that it is the polyol which avoids these deposits (third function of the polyol) and it thus contributes to increasing the yield. Studies seem to show that the three abovementioned functions of the polyol are fulfilled in an optimum manner when substantially between 0.1 and 0.4 mole of polyol are available per mole of cyclic organic carbonate.

The zeolite used is preferably a powder with a mean particle size of between 3 and 5 microns. It is possible advantageously to use between 3.5 and 10.5 g of zeolite per mole of cyclic organic carbonate so that the medium contains a number of catalytic sites which are not limiting for the reaction.

The method of the invention may be employed in a batch manner or continuously or semi-continuously. The continuous or semi-continuous method of operation consists of continuously extracting the epoxide vapors and carbon dioxide formed from the medium. This operating method will be preferred industrially by reason of the advantages to which it leads (higher yield, a saving of catalyst, a reduction in the quantity of byproducts and the high productivity of the installation).

In the semi-continuous method of operation, glycerol carbonate is added during the reaction to compensate for the quantities consumed and to maintain the initial concentration of this compound substantially constant. Polyol is also added during the reaction so as to maintain the proportion of polyol substantially between 0.1 and 0.4 mole of polyol per mole of glycerol carbonate. These additions may be carried out so that the volume of the liquid phase of the reaction medium remains constant so as to obtain a substantially constant production of glycidol. In this semi-continuous method of operation, other constituents of the reaction medium are withdrawn from time to time from the lower part of the reactor.

The continuous method essentially comprises the following operations: a mixture of glycerol carbonate, glycerol and solid catalyst in the form of powder are previously prepared continuously and this mixture is continuously delivered into a thin-film reactor adapted to centrifuge the mixture and to form a revolving peripheral film constituting the reaction medium, vapours of glycidol or a glycidyl compound and the carbon dioxide formed are extracted continuously from the upper part of the reactor, and the other constituents of the medium are extracted continuously from the lower part of the reactor.

Such a method is valuable on the industrial scale by reason of the totally continuous character of the manufacturing process and energy savings due to carrying out the reaction in a rotating thin film.

The invention extends to an installation for implementing the method defined above, characterized in that it comprises in combination:
- means for supplying cyclic organic carbonate,
- means for supplying polyol,
- a closed reactor associated with means of heating and means of stirring and connected to the aforementioned means of supply,
- means for extracting the gaseous phase from the reactor,
- a condenser connected to the extraction means with a view to condensing and separating epoxide from $CO_2$,
- means for recovering the liquid glycidol issuing from the condenser,
- means of pumping, connected to the condenser and able to extract $CO_2$ therefrom and to maintain a predetermined reduced pressure in the installation,
- means for drawing off the constituents from the lower part of the reactor,
- the means of supply, the reactor, the means of extraction, the condenser, the means of recovery and the draw-off means forming a sealed assembly connected to the means of pumping.

The reactor may advantageously be a thin film reactor fitted with a moving device for centrifuging the reaction medium. It should be noted that this type of thin film reactor is known per se for carrying out evaporations, but to the knowledge of the inventors, has never been used for carrying out a reaction, in particular a balanced reaction. This type of reactor which encourages evaporation over all the interface of the thin film contributes to a displacement of the equilibrium of the reaction towards the epoxide.

The following examples illustrate the invention and the performances obtained. These examples were put into operation on installations such as shown diagrammatically in the drawings. In these drawings,

BRIEF DESCRIPTION OF DRAWINGS

FIG. 3 is a diagram of a continuously operating installation, used for implementing example 21, and FIG. 4 is a detailed diagram of the centrifuge of the reactor of this installation.

Figure 1:
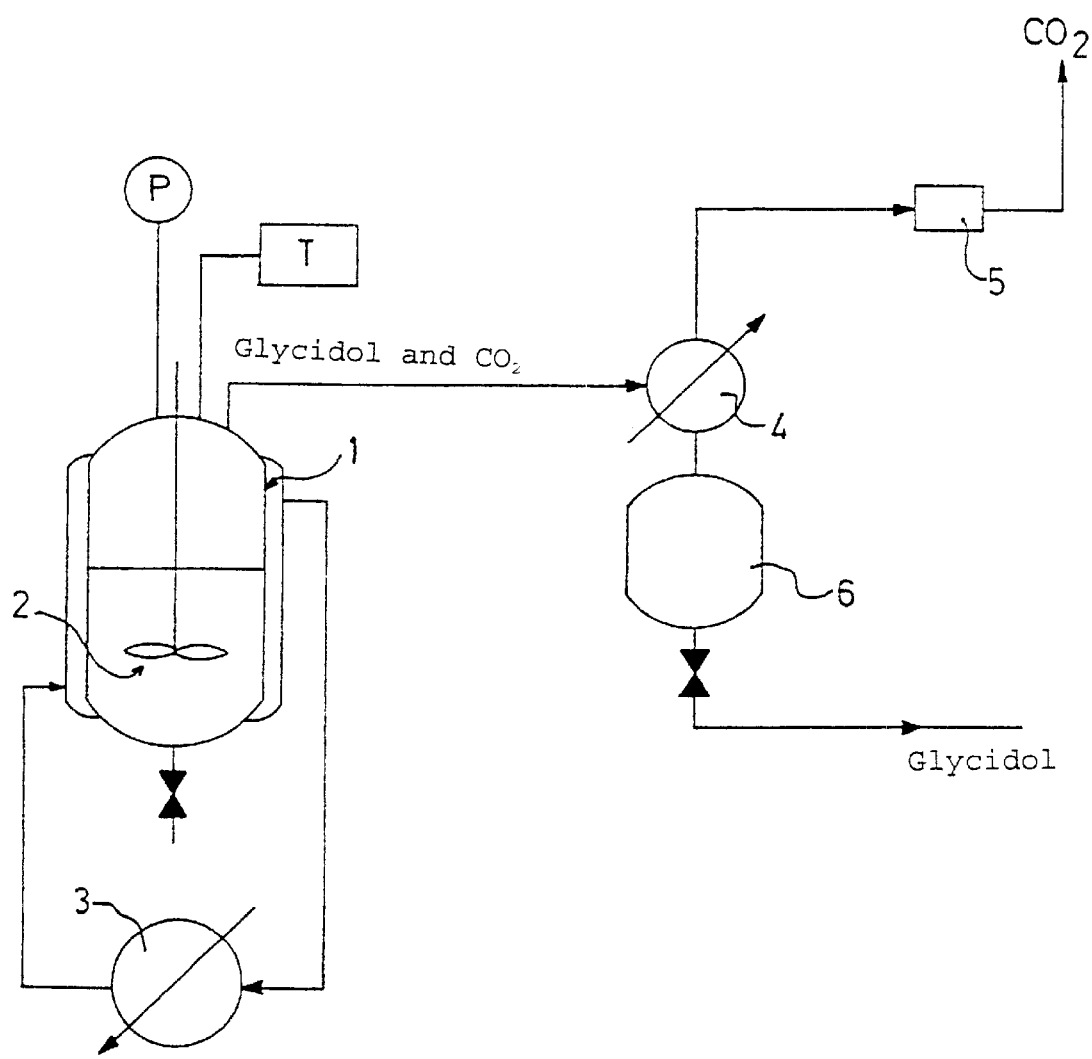
FIG. 1 is a diagram of a discontinuously (batch) operating installation used for implementing examples 1 to 15.

The discontinuously operating installation, shown in FIG. 1, comprises a semi-closed reactor 1 in which a catalyst in the form of a powdered solid and a liquid mixture of glycerol carbonate and glycerol are initially introduced. This reactor is provided with a mechanical stirrer symbolised at 2 and means for heating comprising a liquid heat conveyer circulating in a jacket and held at a suitable temperature by a resistor 3. This reactor is connected by a pipe to a condenser 4 which is associated, on the one hand, with means of pumping 5 enabling the gaseous phase to be extracted and a predetermined reduced pressure to be maintained in the installation and in the reactor 1 and, on the other hand, a flask 6 for recovering the liquid glycidol formed.

Figure 2:
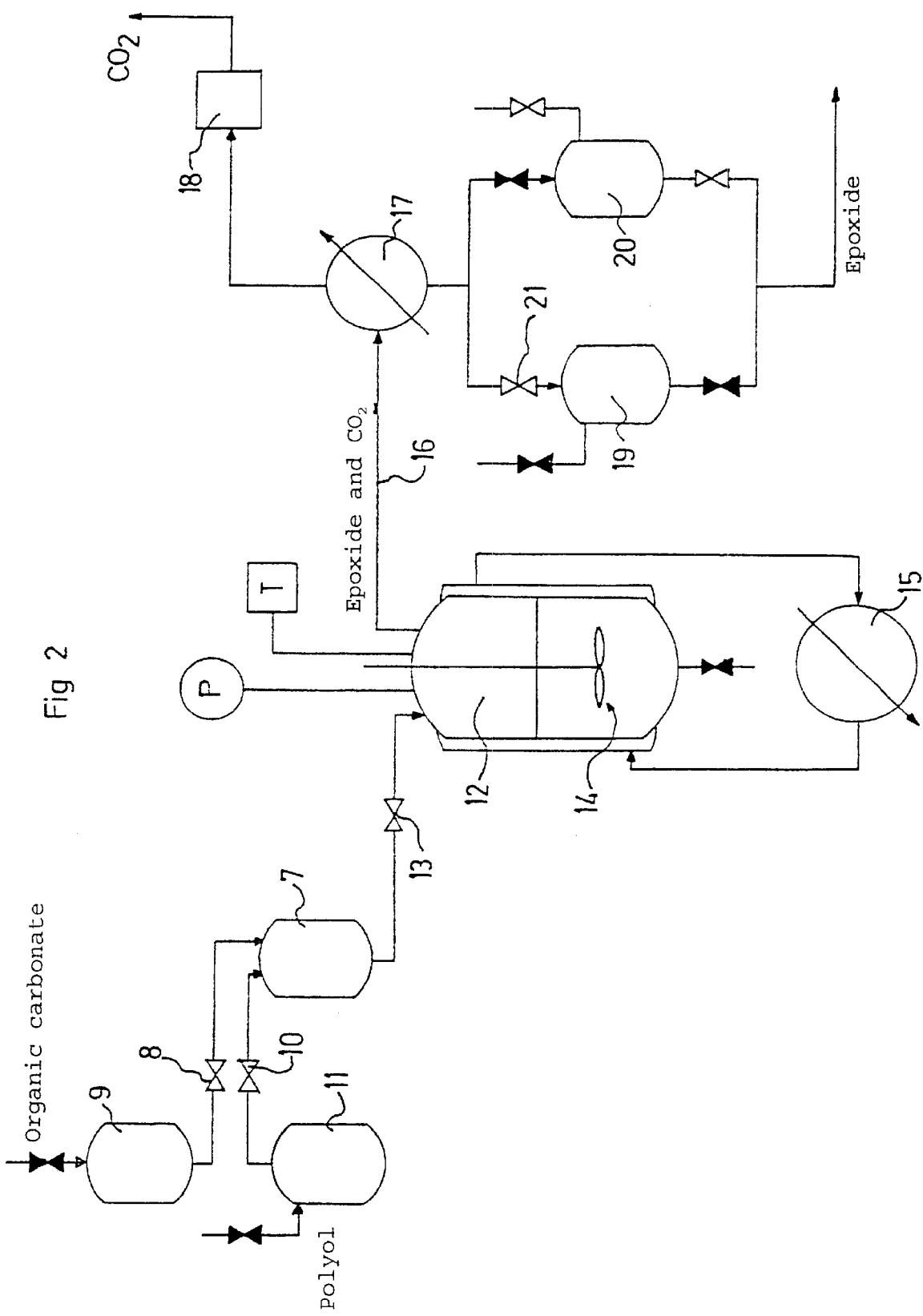
FIG. 2 is a diagram of a semi-continuously operating installation, used for implementing examples 16 to 20.

The semi-continuously operating installation, shown in FIG. 2, comprises a mixer 7 connected on the one hand via metering means 8 to a glycerol carbonate reservoir 9 and, on the other hand, via metering means 10 to a glycerol reservoir 11. The mixer 7 is connected to a reactor 12 via a metering device 13. The reactor 12 is provided with means for stirring symbolized in 14 and means of heating symbolized in 15. As previously, the reactor 12 consists of two envelopes between which a heating fluid circulates which enables its temperature to be regulated. A pipe 16 for extracting the gaseous phase from the reactor emerges in a condenser 17 containing a cooling fluid, this condenser being connected as previously to means of pumping 18 with a view to extracting $CO_2$ and for maintaining a reduced pressure in the installation. Means for recovering the liquid glycidol issuing from the condenser comprise, in this embodiment, two flasks 19 and 20 used alternately by virtue of a set of valves such as 21. The installation forms a sealed assembly connected to the means of pumping 18 so that the desired reduced pressure can be maintained in the said installation.

The continuously operating installation shown in FIGS. 3 and 4 is similar to the semi-continuous installation of FIG. 2 except for the following differences:

The means for continuously supplying a solid catalyst in powder form (hopper 22 and metering device) are provided to deliver an adjustable flow of powdered catalyst into a mixer 23. Metering means 24 thus supply a thin-film reactor 25 with reaction mixture: cyclic organic carbonate, polyol and powdered catalyst, this mixture being present in the form of a colloidal liquid which is easily conveyed.

The reactor 25 is fitted with a centrifuge consisting in a manner known per se of a drive motor M, revolving peripheral discs such as 26 (in the example arranged in three superimposed series, arranged at 120°) and a rotating lower blade 27. The speed of rotation of the centrifuge during operation is 800 rpm and the centrifuge brings about the formation of a thin film (thickness less than mm) against the cylindrical wall of the reactor.

At the base of the reactor, draw-off means enable the constituents of the medium other than gaseous constituents to be extracted continuously. These draw-off means comprise two reservoirs 28 and 29 and valves such as 30 which enable the reservoirs to be emptied in turn, ensuring continuous extraction by gravity at the base of the reactor while keeping the reactor at a reduced pressure.

In the three types of installation (discontinuous, semi-continuous or continuous) the reactor is provided with pressure sensors P and temperature sensors T.

EXAMPLE 1

In the semi-closed container 1 of FIG. 1, 35.4 g (0.3 mole) of glycerol carbonate were mixed with 9.2 g (0.1 mole) of glycerol and 7.2 g of 5A zeolite in the Ca form, in the powdered state, with a mean particle size equal to 4 µm. The reaction mixture was brought to 183° C. and the pressure was lowered to 35 hectopascals with mechanical stirring for 1 hour. During the reaction, glycidol condensed by the condenser was recovered in the flask 6. The impure glycidol recovered was analyzed by gas chromatography on a "Carbowax" 20M (12 m) capillary column with tetraethylene glycol as internal standard. 25.6 g (0.217 mole) of glycerol carbonate were converted into 16.1 g of glycidol, i.e. a molar yield of 72% based on glycerol carbonate.

EXAMPLES 2–5

A series of tests for synthesizing glycidol was carried out using the semi-closed reactor of FIG. 1, in which 35.4 g (0.3 mole) of glycerol carbonate were mixed with 9.2 g (0.1 mole) of glycerol as co-reagent and 7.2 g of catalyst. The reaction was carried out at a pressure of 35 hectopascals. In these examples, the nature of the catalyst was varied.

The operating conditions and the results obtained are assembled in table 1.

TABLE 1

Preparation of glycidol in the presence of different catalysts.

| Number of example | Catalyst | Temperature (° C.) | Duration (h) | Effective yield in glycidol (%)* |
|---|---|---|---|---|
| 2 | 4A Zeolite, Na Powder (3–5 µm) | 183–186 | 1 | 72 |
| 3 | 3A Zeolite, K Powder (3–5 µm) | 183–188 | 1 | 72 |
| 4 | A Zeolite, H Powder (3–5 µm) | 187–190 | 1 | 66 |
| 5 | γ-Al$_2$O$_3$ | 178–186 | 4 | 44 |

*Molar yield in glycidol isolated, based on glycerol carbonate.

EXAMPLES 6–7

A series of tests for synthesizing glycidol was carried out the semi-closed reactor of FIG. 1, in which 35.4 g mole) of glycerol carbonate were mixed with 7.2 g of 5A zeolite as catalyst and 14 g of co-reagent. The operating conditions and the results obtained are assembled in table 2.

TABLE 2

Preparation of glycidol in the presence of different co-reagents.

| Number of example | Co-reagent | Temperature (° C.) | Duration (h) | Yield in glycidol (%)* |
|---|---|---|---|---|
| 6 | Polyethylene glycol | 181–183 | 2 | 41 |
| 7 | Polyglycerol | 189–191 | 1 | 53 |

*Molar yield in glycidol isolated based on glycerol carbonate.

EXAMPLES 8–14

A series of tests for synthesizing glycidol was carried out using the semi-closed reactor of FIG. 1, in which 35.4 g (0.3 mole) of glycerol carbonate were mixed with 5A zeolite and glycerol. The reaction was carried out under partial vacuum. In these examples, variations were made to the quantity of catalyst and glycerol, the temperature and pressure. The operating conditions and results obtained are assembled in table 3.

TABLE 3

| N* of example | Glycerol concentration (%)[1] | Quantity of 5A zeolite (g) | Temperature (° C.) | Pressure (hectopascals) | Duration (h) | Effective yield in glycidol (%)[2] |
|---|---|---|---|---|---|---|
| 8  | 25 | 3.6  | 186–187 | 35 | 1 | 69 |
| 9  | 25 | 10.8 | 185–187 | 35 | 1 | 70 |
| 10 | 25 | 7.2  | 177–178 | 35 | 1 | 68 |
| 11 | 25 | 7.2  | 195–197 | 35 | 1 | 73 |
| 12 | 25 | 7.2  | 182–184 | 25 | 1 | 69 |
| 13 | 25 | 7.2  | 183–186 | 60 | 1 | 68 |
| 14 | 10 | 7.2  | 183–185 | 35 | 1 | 66 |

[1]Molar concentration of glycerol in the reaction mixture.
[2]Molar yield in glycidol isolated, based on glycerol carbonate.

EXAMPLE 15

In the reactor of FIG. 1, 30.6 (0.3 mole) of propylene carbonate were mixed with 10 g (0.06 mole) of diglycerol and 5 g of 5A zeolite in the Ca form, in the powdered state, with a mean particle size equal to 4 $\mu$m. The reaction mixture was brought to 180° C. and the pressure was reduced to 100 mbar with mechanical stirring for 2 hours. During the reaction, propylene oxide condensed by the condenser was recovered in the flask 7. It should be noted that, at the outlet from the reactor 2, care was taken to see that the circuit was free from water so as to prevent the conversion of ethylene oxide into propanediol. The impure propylene oxide recovered was analyzed by gas chromatography. 9.6 g (6 mole) of propylene oxide were recovered, i.e. a molar yield in propylene oxide of 53.3% based on propylene carbonate.

EXAMPLE 16

2.4 g of 5A zeolite, 11.8 g (0.1 mole) of glycerol carbonate and 2.7 g (0.03 mole) of glycerol were initially introduced into the continuous reactor (500 ml) of FIG. 2. The reaction mixture was brought to 183° C. with mechanical stirring for 5 minutes. The reaction was then carried out at 35 hectopascals. A mixture of glycerol carbonate and glycerol was added continuously during the reaction at a feed rate of 1.1 ml/min. The reagents were fed in and the gaseous mixture of glycidol and $CO_2$ were withdrawn continuously for one and a half hours. The glycidol condensed in the condenser was collected in the flasks 17 or 18 of FIG. 2. The glycidol recovered was analyzed by gas chromatography on a "Carbowax" 20M (12 m) capillary column with tetraethylene glycol as internal standard. 59.6 g (0.51 mole) of glycerol carbonate were converted into 37.4 g of glycidol, i.e. a molar yield of 84% based on glycerol carbonate.

EXAMPLES 17–18

A series of tests for synthesizing glycidol was performed using the thoroughly stirred semi-continuous reactor of FIG. 2. The method used was that of example 16. The catalysts studied were: 4A zeolite. Following analysis by GC, the results assembled in table 4 were observed.

TABLE 4

Preparation of glycidol in the thoroughly stirred semi-continuous reactor. Influence of the catalyst.

| Number of example | Catalyst | Temperature (° C.) | Duration (h) | Yield in glycidol (%)* |
|---|---|---|---|---|
| 16 | 4A Zeolite 2.4 g | 183–185 | 1.5 | 83 |
| 17 | 3A Zeolite 2.4 g | 183–185 | 1.5 | 83 |

*Molar yield in glycidol isolated, based on glycerol carbonate.

EXAMPLE 19

A test for synthesizing glycidol was performed using the thoroughly stirred semi-continuous reactor of FIG. 2. The method used was that of example 16. The quantities of reagents introduced during the reaction were: 118 g (1 mole) of glycerol carbonate and 31.3 g (0.34 mole) of glycerol. Following GC analysis of the glycidol isolated, an 86% yield in glycidol isolated was obtained, based on glycerol carbonate.

EXAMPLE 20

A test for synthesizing glycidol was performed using the thoroughly stirred semi-continuous reactor of FIG. 2. The method used was that of example 19. The quantity of 5A zeolite introduced was 4.9 g. Following GC analysis of the glycidol isolated, an 85% yield in glycidol was obtained, based on glycerol carbonate.

EXAMPLE 21

472 g (4 moles) of glycerol carbonate, 73.6 g (0.8 mole) of glycerol and 28 g of A zeolite were mixed in the mixer 23 of the continuous installation of FIG. 3. The reaction mixture was distributed into the reactor at a rate of 20 ml/min by means of the metering device 24. The reaction was carried out in a thin film applied against the cylindrical inner surface of the reactor for 30 minutes. The temperature of the surface of the reactor was held at 190–200° C. by the heat transfer fluid (oil at 230° C.). The reaction was carried out at 35 hectopascals (around 35 mbar). The reagents were fed in, the gaseous mixture of glycidol and $CO_2$, was extracted and the non-gaseous constituents were withdrawn continuously from the bottom of the reactor. The glycidol condensed in the condenser was analyzed by gas chromatography (GC) on a "Carbowax" 20M (12 m) capillary column with tetraethylene glycol as internal standard. A yield of 85% with a purity of 92% was obtained following analysis by GC. The product collected contained 6% glycerol and 2% glycerol carbonate which were entrained by glycidol and $CO_2$.

What is claimed is:

1. A process for preparing an epoxide of the formula:

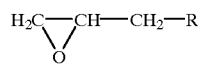

wherein R is hydrogen, hydroxy, alkyl, alkoxy or acyloxy, comprising the steps of:

heating a cyclic organic carbonate of the formula:

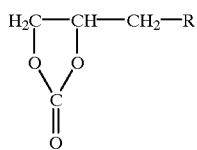

wherein R is as defined above, under reduced pressure to a temperature of at least about 165° C. so as to effect transformation of the carbonate ring into an epoxy ring, wherein said transformation is carried out in a solid/liquid medium in the presence of a polyol and a solid catalyst comprising a type A zeolite or γ-alumina.

2. The process as claimed in claim 1, wherein glycerol or a polyglycerol is used as the polyol.

3. The process as claimed in claim 1, wherein a zeolite in the H form or containing an alkali metal or alkaline earth cation is used as the solid catalyst.

4. The process as claimed in claim 3, wherein said zeolite is mixed into said medium in the form of powder with a mean particle size of between 3 and 5 microns.

5. The process as claimed in claim 3, wherein between 3.5 and 10.5 g of zeolite per mole of cyclic organic carbonate is used.

6. The process as claimed in claim 1, wherein between 0.1 and 0.4 mole of polyol per mole of cyclic organic carbonate is used.

7. The process as claimed in claim 1, wherein the epoxide prepared is glycidol or a glycidyl compound, wherein glycerol carbonate or a glycidyl compound is used as the cyclic organic carbonate and glycerol is used as the polyol.

8. The process as claimed in claim 7, wherein the medium is heated to a temperature between 170° C. and 210° C. and the pressure is adjusted to a value between $3 \times 30^3$ and $10 \times 10^3$ Pascals.

9. The process as claimed in claim 8, wherein the pressure is adjusted to a value between $3.3 \times 10^3$ and $6 \times 10^3$ Pascals.

10. The process as claimed in claim 7, further comprising the steps of:

extracting vapors formed of glycidol or glycidyl compound and carbon dioxide from the medium, and separating the glycidol or glycidyl compound by condensation.

11. The process as claimed in claim 10, further comprising the steps of:

adding glycerol carbonate to the medium to maintain an initial glycerol carbonate concentration, and adding polyol to keep the proportion of polyol between 0.1 and 0.4 mole of polyol per mole of glycerol carbonate.

12. The process as claimed in claim 10, further comprising the steps of:

delivering a mixture of glycerol carbonate, glycerol and solid catalyst in powder form into a thin-film reactor adapted to centrifuge the mixture and to form a revolving peripheral film;

extracting the medium, vapors of glycidol or a glycidyl compound and a resultant carbon dioxide formed from an upper part of the reactor; and extracting the other constituents of the medium from a lower part of the reactor.

* * * * *